US011129551B2

(12) United States Patent
Noh et al.

(10) Patent No.: US 11,129,551 B2
(45) Date of Patent: Sep. 28, 2021

(54) METHOD FOR PROVIDING AGE-RELATED GAIT MOTION TRASNFORMATION BASED ON BIOMECHANICAL OBSERVATIONS AND AN APPRATUS USING IT

(71) Applicant: KOREA ADVANCED INSTITUTE OF SCIENCE AND TECHNOLOGY, Daejeon (KR)

(72) Inventors: Junyong Noh, Daejeon (KR); Sunjin Jung, Daejeon (KR); Seokpyo Hong, Daejeon (KR); Kyungmin Cho, Daejeon (KR); Haegwang Eom, Daejeon (KR); Byung Kuk Choi, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 351 days.

(21) Appl. No.: 16/015,474

(22) Filed: Jun. 22, 2018

(65) Prior Publication Data

US 2018/0368734 A1 Dec. 27, 2018

(30) Foreign Application Priority Data

Jun. 23, 2017 (KR) .................. 10-2017-0079893

(51) Int. Cl.
*A61B 5/11* (2006.01)
*A61B 5/103* (2006.01)
(Continued)

(52) U.S. Cl.
CPC ............ *A61B 5/112* (2013.01); *A61B 5/1038* (2013.01); *A61B 5/1071* (2013.01);
(Continued)

(58) Field of Classification Search
CPC ..... A61B 5/112; A61B 5/1038; A61B 5/1071; A61B 5/1077; A61B 5/1107; A61B 5/1116; A61B 5/1121; A61B 5/0077; A61B 5/163; A61B 5/4082; A61B 5/162; A61B 3/113; A61B 5/1036; G09B 19/003; G06Q 10/10; G06Q 50/10; G06T 13/80; G06T 13/00;
(Continued)

(56) References Cited

U.S. PATENT DOCUMENTS

2016/0338621 A1* 11/2016 Kanchan ................ A61B 5/002

OTHER PUBLICATIONS

Jean-Sebastien Monzani, Paolo Baerlocher, Ronan Boulic and Daniel Thalmann "Using an Intermediate Skeleton and Inverse Kinematics for Motion Retargeting" EUROGRAPHICS 2000 / M. Gross and F.R.A. Hopgood vol. 19 (2000), No. 3 (Year: 2000).*

(Continued)

*Primary Examiner* — David J. McCrosky
*Assistant Examiner* — Chanel J Jhin

(57) ABSTRACT

An apparatus for motion transformation according to an embodiment of the present disclosure includes a basic data input unit through which basic motion data is inputted, a pre-processing unit which acquires a parameter through pre-processing of the inputted basic motion data, a motion transformation unit which performs biomechanical observations-based gait motion transformation processing based on the pre-processed parameter and age input information, and an output unit which outputs the transformation processed motion.

15 Claims, 7 Drawing Sheets

(51) Int. Cl.
*A61B 5/107* (2006.01)
*G06T 7/269* (2017.01)
*G06T 7/262* (2017.01)
*G06T 7/215* (2017.01)
*A61B 5/00* (2006.01)

(52) U.S. Cl.
CPC .......... *A61B 5/1077* (2013.01); *A61B 5/1107* (2013.01); *A61B 5/1116* (2013.01); *A61B 5/1121* (2013.01); *G06T 7/215* (2017.01); *G06T 7/262* (2017.01); *G06T 7/269* (2017.01); A61B 5/0077 (2013.01)

(58) Field of Classification Search
CPC .......... G06T 13/20; A63F 13/30; A63F 13/06; A63F 13/21; H04H 60/65; H04N 21/42201; G05B 15/02; G05B 19/0426; B62D 57/032; G06F 3/048; G06F 3/013; G16H 50/50; G16H 50/20; G10L 15/22; G06K 9/00335; G06K 9/00369; G06K 9/00342; A61N 1/0548; A61N 1/36103; A63B 24/0062; A63B 24/0003; A63B 71/0622; H04M 1/72563

USPC ....................................................... 600/595
See application file for complete search history.

(56) References Cited

OTHER PUBLICATIONS

Daseong Han et al., "Online Real-time Locomotive Motion Transformation Based on Biomechanical Observations", *Computer Animation and Virtual Worlds*, vol. 28 (May 2017) pp. 1-9.

Chathika Gunaratne et al., "Simulating Gait and Structural Effects of Aging for Improved Diversity in Virtual Crowds", *Computer Graphics, Imaging and Visualization*, (2013) pp. 17-22.

Dinh Duy Le et al., "Integrating Age Attributes to Virtual Human Locomotion", *International Archives of the Photogrammetry. Remote Sensing and Spatial Information Sciences*, (2003) pp. 1-5.

Yoonsang Lee et al., "Performance-Based Biped Control using a Consumer Depth Camera", *Computer Graphics Forum*, vol. 26, No. 2 (May 2017) pp. 387-395.

\* cited by examiner (a)

(b)

(a)          (b)

METHOD FOR PROVIDING AGE-RELATED GAIT MOTION TRASNFORMATION BASED ON BIOMECHANICAL OBSERVATIONS AND AN APPRATUS USING IT

CROSS-REFERENCE TO RELATED APPLICATION

This application claims priority of Korean Patent Application No. 10-2017-0079893, filed on Jun. 23, 2017, in the KIPO (Korean Intellectual Property Office), the disclosure of which is incorporated herein entirely by reference.

BACKGROUND OF THE INVENTION

Field of the Invention

The present disclosure relates to an apparatus and method for providing motion transformation. More particularly, the present disclosure relates to a method and apparatus for providing age-related gait motion transformation processing based on biomechanical observations.

Description of the Related Art

Studies on automatic generation of human gait motions have been intensively made. In particular, recently with development of data processing technology, data based motion reproduction technique involving data organization and synthesis of human body motions is emerging. Currently, this technique aims at implementing an interface which accurately measures the velocity and rotational angle of each part of a human body according to the motion type, and provides human body motions synthesized in real time by an online method on the premise that the motions will be reproducibly transformed in the future.

Particularly, this interface can be currently applied to virtual characters that appear in computer animations, films or games, but a problem which has arisen is that it is necessary to apply age-related changes. For example, a character becomes older and older as the story goes. Sometimes, the character may become younger. In this case, the appearance or motions need to be changed appropriately for the changed age.

To solve this, age-related character simulations have been intensively studied, but most of them focus on facial aging simulations, and the motion issue has not been discussed so much.

For this reason, technology has been using fundamental methods including key framing or motion capture, and it has a disadvantage that it is a human-operated task, requiring much time, it is impossible to immediately capture age-related motions of one person, and capture should be continuously repeated for a target age.

Accordingly, there is an urgent need for automatic transformation to apply kinetic features to a character's motions with reflecting different ages.

SUMMARY OF THE INVENTION

The present disclosure is designed to solve the above-described problem, and therefore the present disclosure is directed to providing a method and apparatus for providing age-related gait motion transformation based on biomechanical observations in which motion transformed data corresponding to natural age-related gait motions can be only generated from basic motion data input, and accordingly age-related gait motions of a human body can be automatically transformation processed into motions of richer and more natural quality.

An apparatus for gait motion transformation according to an embodiment of the present disclosure for solving the above-described problem includes a pre-processing unit which performs pre-processing corresponding to inputted basic motion data, an age input unit, a motion transformation unit which performs biomechanical observations-based gait motion transformation processing stepwise according to age input from the age input unit, and an output unit which outputs the transformation processed motion.

Additionally, a method for gait motion transformation according to an embodiment of the present disclosure for solving the above-described problem includes performing pre-processing corresponding to inputted basic motion data, receiving an input of age, performing biomechanical observations-based gait motion transformation processing stepwise according to the age input, and outputting the transformation processed motion.

Meanwhile, the method according to an embodiment of the present disclosure for solving the above-described problem may be recorded in a program for executing the method and implemented in a computer-readable recording medium.

According to the embodiments of the present disclosure, there is provided a method and apparatus for providing age-related gait motion transformation based on biomechanical observations in which motion transformed data corresponding to natural age-related gait motions can be only generated from basic motion data input, and accordingly age-related gait motions of a human body can be automatically transformation processed into motions of richer and more natural quality.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
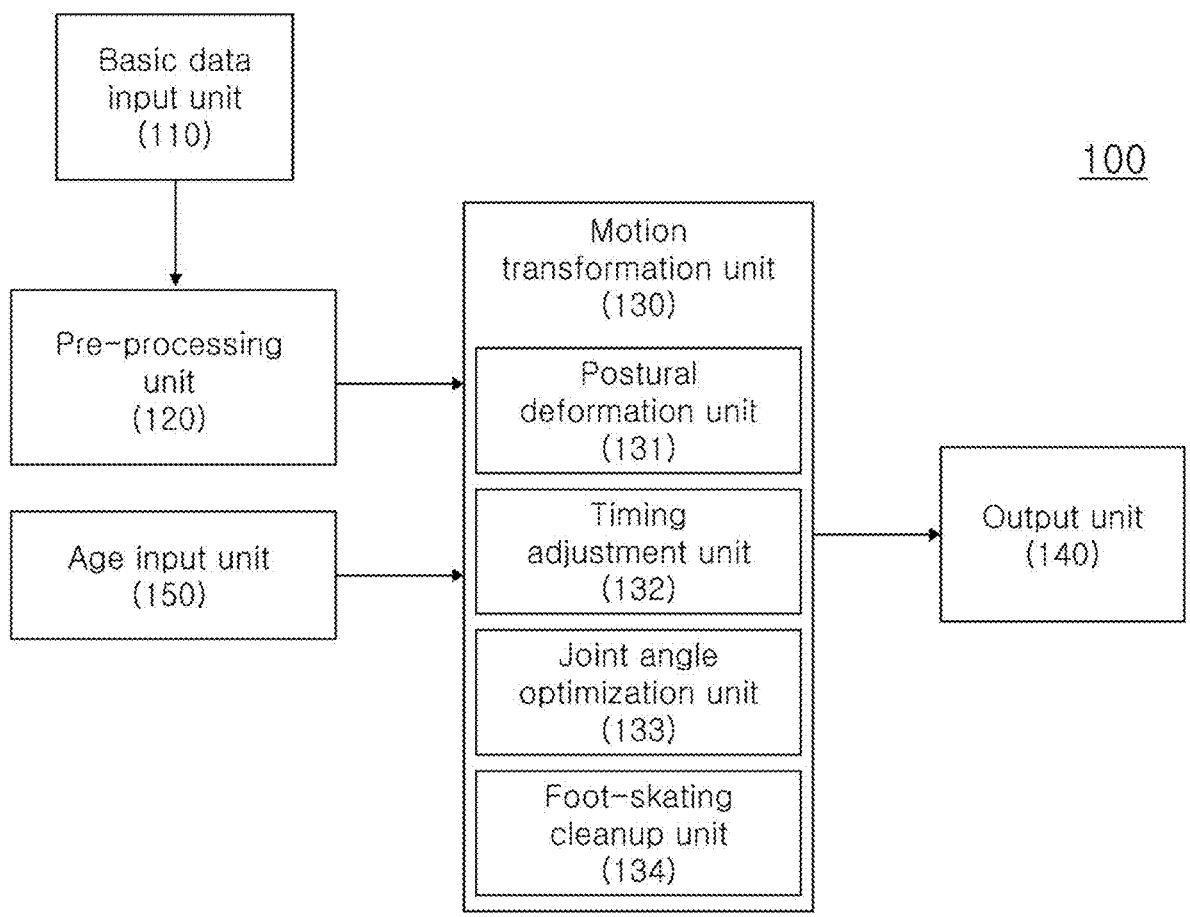
FIG. 1 is a block diagram showing the entire system and a motion transformation apparatus according to an embodiment of the present disclosure.

The following description provides the principle of the present disclosure for illustration only. Although not explicitly described or depicted herein, persons having ordinary skill in the art will be able to implement the principle of the present disclosure and invent various devices included in the concept and scope of the present disclosure. In addition, it should be understood that all the conditional terms and embodiments enumerated in the present disclosure are, in principle, intended to help a full understanding of the concept of the present disclosure, but not being limited to the embodiments and states particularly described.

In addition, it should be understood that the fully detailed description that enumerates the principle, perspective and embodiments of the present disclosure as well as specific embodiments is intended to include structural and functional equivalents thereto. It should be further understood that these equivalents include all elements invented to perform the same function no matter whether the equivalents or structures are currently known or will be developed in the future.

Therefore, it should be understood that a block diagram in the specification shows the conceptual perspective of an exemplary circuit to embody the principle of the present disclosure. In a similar way, all flowcharts, state transition diagrams and pseudocodes may be substantially represented in computer readable media and should be understood as representing various processes that are executed by a computer or processor irrespective of whether the computer or the processor is clearly illustrated or not.

The functions of various elements depicted in the drawings including the processor or functional block represented on the similar concept may be provided by use of exclusive hardware as well as hardware having the capability of executing software in relation to appropriate software. When they are provided by the processor, the above-described functions may be provided by a single exclusive processor, a single shared processor or a plurality of individual processors, and some of them may be shared.

In addition, the explicit use of processor, control or term presented on the similar concept should not be interpreted as exclusively citing hardware having the capability of executing software, and it should be interpreted as implicitly including, but not limited to, digital signal processor (DSP) hardware and ROM, RAM and nonvolatile memory for storing software. Other well-known hardware may be included.

In the appended claims, the components expressed as means for executing the function described in the detailed description are intended to include, for example, all methods for executing functions including all types of software including a combination of circuit elements performing the above-described functions or firmware/microcode and they are combined with an appropriate circuit for executing the software to execute the functions. Because the functions provided by various enumerated means are combined and they are combined in a way that the claims require, the present disclosure defined by the appended claims should be understood that any means for providing the above-described functions is equivalent to what is comprehended from the specification.

The above-described objects, features and advantages will be apparent through the following description in relation to the accompanying drawings, and accordingly, persons having ordinary skill in the art to which the present invention pertains will easily practice the technical spirit of the present disclosure. Additionally, in the description of the present disclosure, when a detailed description of known technology in relation with the present disclosure is deemed to render the subject matter of the present disclosure unnecessarily ambiguous, its detailed description is omitted herein.

Hereinafter, a preferred embodiment according to the present disclosure will be described in detail with reference to the accompanying drawings.

Figure 2:
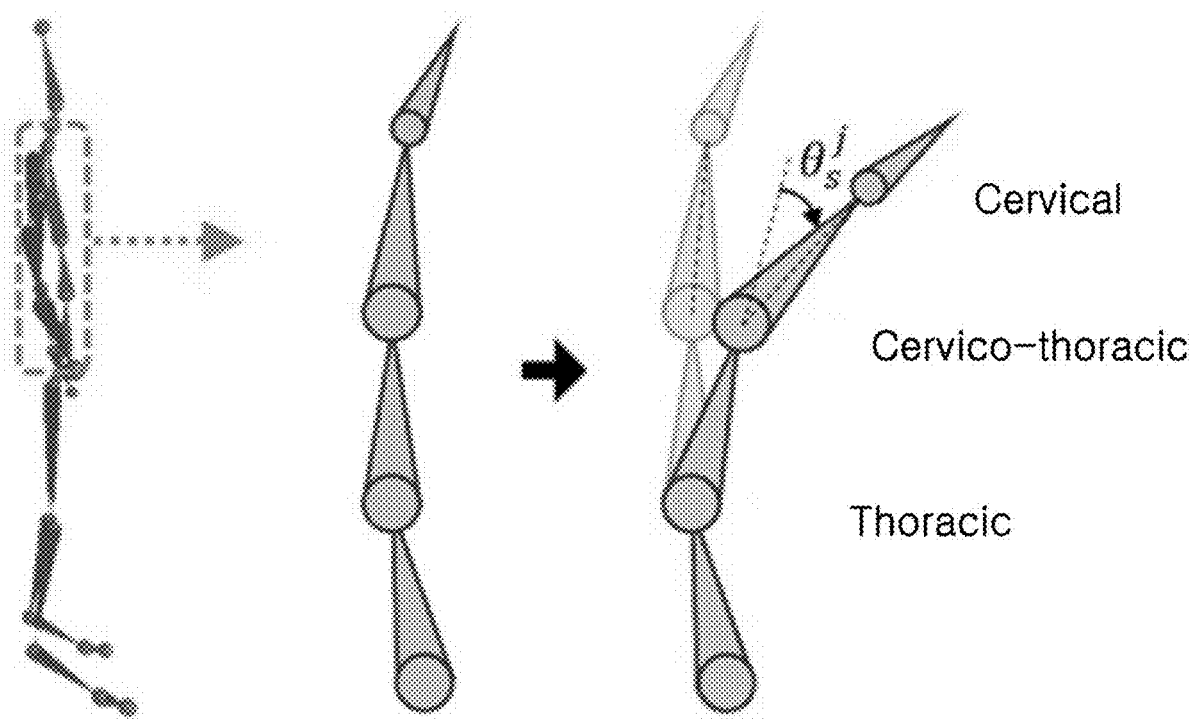
FIG. 2 is a diagram illustrating age-related motion according to an embodiment of the present disclosure.

FIG. 1 is a schematic conceptual diagram of the entire system according to an embodiment of the present disclosure, and FIG. 2 is a diagram illustrating age-related motion according to an embodiment of the present disclosure.

Referring to FIG. 1, the system according to an embodiment of the present disclosure may constitute a motion transformation apparatus 100, and may output motion transformed-motion data according to age input, based on basic motion data. To this end, the motion transformation apparatus 100 includes a basic data input unit 110, a pre-processing unit 120, an age input unit 150, a motion transformation unit 130 and an output unit 140.

Basically, the motion transformation apparatus 100 according to an embodiment of the present disclosure may transform a basic dynamic motion based on biomechanics according to age information input, and output it as a natural motion that is suited for the age.

To this end, when an original motion is inputted through the basic data input unit 110, the pre-processing unit 120 may segment a gait motion of a given character by each gait cycle.

Additionally, with the age information inputted through the age input unit 150, the motion transformation unit 130 may perform stepwise motion transformation processing using each motion transformation module of a postural deformation unit 131, a timing adjustment unit 132, a joint angle optimization unit 133 and a foot-skating cleanup unit 134 to finally generate motion data corresponding to the age, and output it to a display device or an external device through the output unit 140.

In an embodiment of the present disclosure, stepwise motion transformation may be described in four overall steps.

The postural deformation unit 131, the timing adjustment unit 132 and the joint angle optimization unit 133 perform processing of 1-3 steps to calculate an angle or speed to rotate the joint of the character upon motion transformation corresponding to the age input.

More specifically, the postural deformation unit 131 may perform postural deformation processing to transform spine information of the motion data according to the age.

Additionally, the timing adjustment unit 132 may perform timing adjustment processing to adjust the speed and time information of double support phase where both feet contact the ground according to the age.

Subsequently, the joint angle optimization unit 133 may perform joint angle optimization to adjust the angle of the joint to an optimized angle.

Here, the joint angle optimization unit 133 may define an objective function of the optimization problem as a function consisting of a total of three energy terms, and calculate a corresponding optimization value, thereby calculating optimized joint angle information. For example, the objective function may include the term (Ea) for adjusting the corresponding joint angle to the age, the term (Ep) for preventing an abrupt change from the existing motion, and in the last place, the term (Es) for smoothly connecting changes in continuous frames, and this will be described below in more detail.

Meanwhile, the foot-skating cleanup unit 134 may perform cleanup processing of a foot-skating problem known as a phenomenon as if a foot slips when gait data is represented, by use of inverse kinematics techniques.

Accordingly, gait data reflecting the curved spine, reduced stride length and transformed angle of each joint appropriately for the input age information compared to the basic motion data may be outputted from the gait data outputted through the output unit 140.

Accordingly, the motion transformation apparatus 100 according to an embodiment of the present disclosure has capability of executing in real time at 32.14 frames/sec on average as a result of experiment with various motion data, thereby achieving real-time transformation processing.

Hereinafter, the entire operation of the motion transformation apparatus 100 for implementing this will be described in more detail.

First, when original basic motion data is inputted through the basic data input unit 110, the pre-processing unit 120 may extract a gait cycle from the basic motion data, and acquire various parameter information about functions that can be observed in each gait cycle including duration of double support phase and peak angle of each joint.

Here, the gait cycle may be defined as a cycle from the moment when a foot contacts the ground to the moment when the same foot contacts the ground again.

Additionally, when age information is inputted through the age input unit 150 and gait cycle information and its corresponding parameter information are acquired through the pre-processing unit 120, the motion transformation unit 130 may perform a motion transformation process to process each module in sequential order according to the gait cycle information and the parameter information.

For example, referring to FIG. 2, human body joint composed of cervical, cervico-thoracic and thoracic may increases in angle with increasing age. Accordingly, first, the postural deformation unit 131 may perform processing to deform the spinal posture of the character according to the inputted age.

Prior to data processing as described below, the parameters of the motion data may be defined as the following Equation 1.

$$M(t) = (p_t^0, q_t^0, q_t^1, \ldots, q_t^{N_j-1})$$ [Equation 1]

Here, $p_t^0 \in \mathbb{R}^3$ may be a 3-dimensional vector, and a unit quarternion $q_t^0 \in \mathbb{S}^3$ may denote the transform orientation of the root joint, and $p_t^j \in \mathbb{S}^3$ may denote the orientation of $j^{th}$ joint.

Here, $1 \leq j < N_j$, and $N_j$ may denote the number of joints.

The postural deformation unit 131 may perform first processing of the motion transformation process according to the parameters to deform the posture of the character according to the inputted age.

Many biomechanical studies analyze the characteristics of neutral posture and reveal age-related posture changes using spinal curvature. Particularly, as humans get older, the spine tends to bend forward. The old people have forward head posture, and may increase in lower cervical flexion angle and upper cervical extension angle compared to those of young people.

Based on these biomechanical observations, the postural deformation unit 131 may deform posture data by rotating the spinal joint composed of cervical, cervico-thoracic and thoracic.

To this end, the postural deformation unit 131 may perform processing disclosed by the following Equation 2.

$$\theta_s^j = \Delta\Theta_s^j \cdot d_{age},$$

$$q_t^{j'} = q_t^j \exp(\theta_s^j \cdot n_s/2).$$ [Equation 2]

Here, $\theta_s^j$ may denote the angle of $j^{th}$ spinal joint to rotate according to the age, as shown in FIG. 2. Additionally, $\Delta\Theta_s^j$ may denote an angle change value based on a table of age-related joint angle changes as shown in the following Table 1.

TABLE 1

| $\Delta\Theta_s^{cervical}$ | $\Delta\Theta_s^{cervico-thoracic}$ | $\Delta\Theta_s^{thoracic}$ |
|---|---|---|
| +0.1573 | −0.273 | −0.6628 |

Referring to well-known Boyle's work, to obtain information about the spine over a wide range of ages, 172 radiographic images have been analyzed. Accordingly, analysis data changing linearly with age can be acquired, and the postural deformation unit 131 may generate a table such as Table 1 based on analysis data, and perform linear transformation processing using the same.

Additionally, d_age may denote a difference between the inputted age information and age information of the basic motion data.

$q_t^j$ and $q_t^{j'}$ may denote the primary orientation and the rotated orientation of $j^{th}$ spinal joint at time t. $n_s$ may denote the axis of rotation of the spinal joint, and it is a direction perpendicular to the sagittal plane and may represent a direction extending from the paper.

Meanwhile, the timing adjustment unit 132 may perform timing adjustment processing of the gait speed and the double support phase according to the age.

Humans reduce in gait speed linearly as they age irrespective of gender or impairment. Based on this observation, using linear interpolation processing between an average gait speed of old people and gait speed of reference data, the annual rate of decline in gait speed may be calculated. According to Prince's study, the annual rate of decline may be selected as a reasonable value in the range of 0.1%-0.7%, and the timing adjustment unit 132 may preferably set an appropriate annual rate of decline for calculation to 0.3%.

The timing adjustment unit 132 may adjust the gait speed by transforming the root trajectory of basic data using the set annual rate of decline.

As parameters for gait speed adjustment, y axis-coordinate and root position coordinates of root joint projected onto the ground are as shown in the following Equation 3.

$$_{zx}p_0 = _{zx}p_0^0,$$

$$_{zx}p_t^{0'} = _{zx}p_{t-1}^{0'} + (1 - \alpha \cdot d_{age})(_{zx}p_t^0 - _{zx}p_{t-1}^0).$$ [Equation 3]

Here, $zxPt^{0'}$ may be the projected position of root joint at time t, and $\alpha \sim N(0.003, 0.0013^2)$ may denote the annual rate of decline in gait speed calculated by biomechanical observations.

Figure 3:
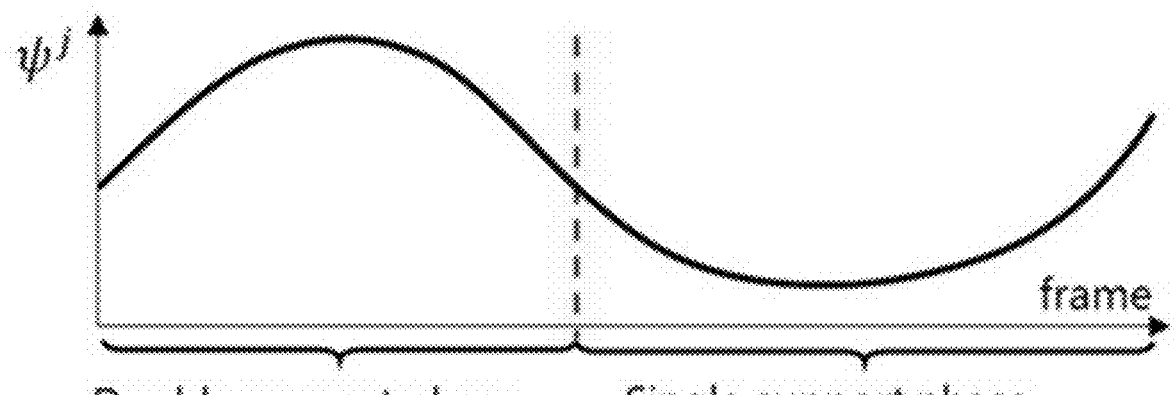
FIG. 3 is a graph illustrating timing adjustment according to an embodiment of the present disclosure.
Figure 3:
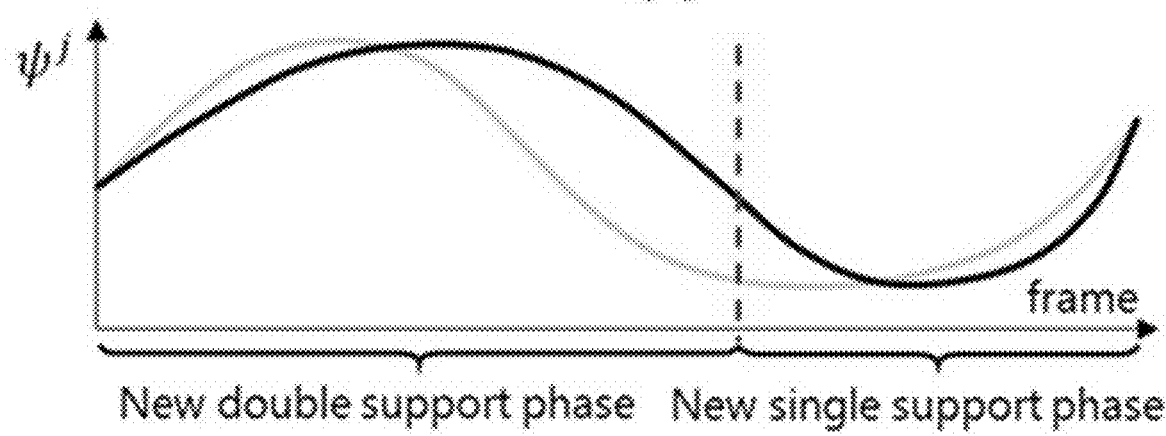

Meanwhile, FIG. 3 is a graph illustrating timing adjustment according to an embodiment of the present disclosure, FIG. 3(a) shows the original phase and joint trajectory, and FIG. 3(b) shows the adjusted phase and joint trajectory.

The timing adjustment unit 132 may perform timing adjustment in double support phase as shown in FIG. 3.

FIG. 3 shows phase adjustment between double support phase and single support phase with aging, and the red dash line may indicate the boundary between the two phases. Accordingly, each phase changes, but the total cycle duration may be equally maintained.

More specifically, the double support phase may be defined as a period during which both feet contact the ground in the gait cycle. As humans get older, they tend to rely on increased double support phase for stability, while the total duration of gait cycle does not change.

Accordingly, referring to FIG. 3, the joint trajectory $\Psi j$ is conceptually shown, and may be an arbitrary feature parameter such as angle, speed or position of the specific joint j. To modify the shape of the trajectory $\Psi j$ appropriately for the adjusted phase, the timing adjustment unit 132 may apply time warp to Ψj in each phase.

When the previously described age difference value d_age, and the number of frames necessary for new double support phase is nd', it may be calculated by the following Equation 4.

$$n^{d'} = n^d + \left(\beta \cdot \left(\frac{r^d}{\tilde{r}^d}\right) \cdot d_{age}\right) \cdot n^c. \quad \text{[Equation 4]}$$

Here, $n^d$ and $n^c$ may denote the number of frames associated with the double support phase and the gait cycle respectively, and $r^d$ may denote a frame ratio. $\sim r^d$ may be the annual rate of decline β~N(0.1475, 0.002^2) calculated in the related essay (David A Winter, Aftab E Patla, James S Frank, and Sharon E Walt. Biomechanical walking pattern changeselb91 in the fit and healthy elderly. Physical therapy, 70(6):340-347, 1990.), and a ratio of $r^d$ and $\sim r^d$ may be applied as a variable.

Figure 4:
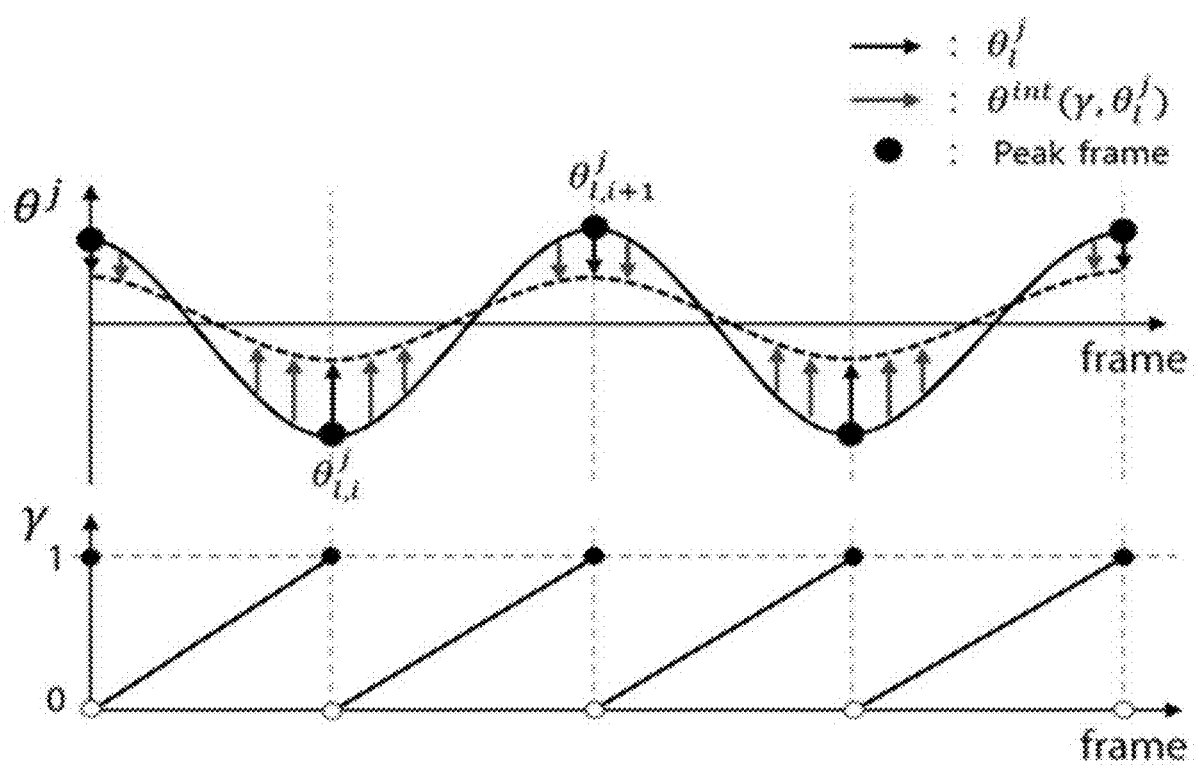
FIG. 4 is a graph illustrating joint angle optimization according to an embodiment of the present disclosure.

FIG. 4 is a graph illustrating joint angle optimization according to an embodiment of the present disclosure.

As shown in FIG. 4, the joint angle optimization unit 133 may perform joint angle optimization processing by angle changes and interpolation of parameters.

Most of biomechanical studies focus primarily on changes in peak extension or flexion angle of each joint with aging. Particularly, according to Kerrigan et al., it reveals that as humans get older, the ankle joint angle, hip joint extension angle and anterior pelvic tilt have statistically significant influence on gait motion. Specifically, because old people have low strength of plantar flexion ankle muscles, they tend to have smaller ankle plantarflexion angle than young people.

In a similar way, old people may reduce in peak hip flexion angle due to hip flexor contracture (muscle contraction). Because the hip flexor contracture also causes anterior pelvic tilt, the pelvic tilts more anteriorly at the peak hip extension angle.

However, even though this individual function is applied to each joint, visually natural motions may not be generated. To accomplish representation of natural age-related motions reflecting all observations, the joint angle optimization unit 133 may formulate the full body optimization problem as an objective function, and compute to find optimized natural motions.

Here, the joint angle optimization unit 133 may set an objective function including the term (Ea) for adjusting the corresponding joint angle to the age, the term (Ep) for preventing an abrupt change from the existing motion, and in the last place, the term (Es) for smoothly connecting changes in continuous frames, and calculate an optimization value using each corresponding weight. The objective function is as shown in Equation 5.

$$\underset{x_t}{\arg\min} \; \omega_A E_A(x_t) + \omega_P E_P(x_t) + \omega_S E_S(x_t), \quad \text{[Equation 5]}$$

Here, w may denote the weight of each term, and $x_t \in \mathbb{R}^{3N_j+3}$ may denote a displacement map showing a difference between two movements described in the essay "Andrew Witkin and Zoran Popovic. Motion warping. In Proceedings of the 22nd annual conference on Computer graphics and interactive techniques, pages 105-108. ACM, 1995." and the essay "Jehee Lee and Sung Yong Shin. A hierarchical approach to interactive motion editing for human-like figures. In Proceedings of the 26th annual conference on Computer graphics and interactive techniques, pages 39-48. ACM Press/Addison-Wesley Publishing Co., 1999."

The displacement map may be defined by the following Equation 6.

$$x_t = M(t)' \Theta M(t) = (u_t^0, v_t^0, v_t^1, \ldots, v_t^{N_j-1}), \quad \text{[Equation 6]}$$

Here, the vector $u_t^0 \in \mathbb{R}^3$ and the expotential map $V_t^0 \in \mathbb{R}^3$ may be translation and rotation displacement of the root joint, and $V_t^{j*} \in \mathbb{R}^3$ for $1 \le j < N_j$ may denote the rotation displacement of $j^{th}$ joint. M(t) may denote motion data processed up to double support phase transformation through the timing adjustment unit 132.

A new motion $M(t)' = M(t) \oplus x_t$ may be acquired by the translation and rotation displacement, and may include optimized computation results. Additionally, the element of M(t)' may be updated according to the following Equation 7

$$p_t^{0'} = p_t^0 + u_t^0,$$

$$q_t^{j'} = q_t^j \exp(v_t^j/2)(0 \le j < N_j). \quad \text{[Equation 7]}$$

In the age-related joint angle constraint (Ea), FIG. 4 shows periodic repeating motion according to the gait cycle at the continuous peak angle for each joint of the articulated body.

Referring to the top of FIG. 4, an example of joint angle changes over time can be seen. The black points indicate a frame in which the joint has a peak extension angle, and this may be called a 'peak frame'.

To obtain a desired angle change in each frame, first, the joint angle optimization unit 133 may calculate a desired angle change for each peak frame as shown in Equation 8.

$$\theta_i^j = \Delta\Theta_i^j \cdot d_{age} \cdot \theta_r^j. \quad \text{[Equation 8]}$$

Similar to Equation 1, $\Delta\Theta_i^j$ denotes an annual angle change, and may be acquired from reference data in Table 2 preset according to the biomechanical observations-based study. Because periodic patterns of human joints show similar tendencies for different amplitudes, $\theta_r^j$ may be set as domain.

TABLE 2

| $\Delta\Theta_i^{ankle}$ | $\Delta\Theta_i^{hip}$ | $\Delta\Theta_i^{APT}$ |
|---|---|---|
| −0.1199 | −0.1516 | +0.0604 |

Accordingly, with the angle change in peak frame of $\theta_i^j$, the joint angle optimization unit 133 may calculate an angle change of each frame between each adjacent peak frame by the following Equation 9.

$$\theta^{int}(\gamma, \theta_i^j) = (1-\gamma) \cdot \theta_{I,i}^j + \gamma \cdot \theta_{I,i+1}^j. \quad \text{[Equation 9]}$$

Here, $\theta^{int}(\gamma, \theta_i^j)$ may denote a linearly interpolated angle change between two continuous peak frames, and may be shown as a region indicated by the red arrow on top of FIG. 4. $\gamma \in (0, 1]$ may be the parameter for linear interpolation.

As shown in FIG. 4, $\theta_{I,i}^j$ and $\theta_{I,i+1}^j$ may denote an $i^{th}$ peak angle change, and a peak angle change of the next peak frame. Additionally, similar to processing at the postural deformation unit 131, the joint angle optimization unit 133 may calculate desired orientation $q_t^{j'}$ by calculating the following Equation 10.

$$q_t^{j'} = q_t^j \exp(\theta^{int}(\gamma, \theta_i^j) \cdot n_I/2), \quad \text{[Equation 10]}$$

Here, $q_t^{j'}$ may denote the orientation of $j^{th}$ limb joint, and $n_l$ may denote the axis of rotation of limb joint, and may be a direction perpendicular to the sagittal plane. The orientation of $n_l$ may be opposite to the above-described orientation of $n_s$.

Accordingly, the joint angle optimization unit 133 may calculate the age-related joint angle optimization variable term $E_A$, and this may be acquired by Equation 11.

$$E_A(x_t) = \sum_{j \in J} \| q_t^{j'} - q_j(x_t) \|^2 .$$  [Equation 11]

Here, $q_j(x_t)$ denotes the orientation of $j^{th}$ joint updated by the displacement map xt. J=(ankle; hip; shoulder; root) may represent a preset joint set. For natural swing motion processing of upper limb, the joint angle optimization unit 133 may set a swing range of upper limb corresponding to a predetermined ratio to a change angle of lower limb. This selection is simple but actually works quite well.

Meanwhile, the joint angle optimization unit 133 may apply penalty to great displacement by computing the term Ep. If the transformed motion deviates from the original motion too much, the feature of the original motion may be damaged, so it is desirable to avoid great displacement of a predetermined value or more for each time t. Accordingly, the joint angle optimization unit 133 may perform penalty processing of great displacement from the transformed motion from the timing adjustment unit 132 as below.

$$E_p(x_t) = \|x_t\|^2.$$  [Equation 12]

Additionally, the joint angle optimization unit 133 may perform computation processing of the term Es for continuous temporal smoothness. An irregular change in two continuous frames may also cause an abnormal or discontinuous movement. To avoid this, the joint angle optimization unit 133 may minimize a time displacement difference by performing computation processing of the term Es as below.

$$E_S(x_t) = \|x_{t-1} - x_t\|^2.$$  [Equation 13]

Meanwhile, the foot-skating cleanup unit 134 performs foot-skating cleanup processing from the optimized motion data outputted from the joint angle optimization unit 133.

The motion transformation on kinetic level may cause foot-skating artifact. Accordingly, the foot-skating cleanup unit 134 according to an embodiment of the present disclosure may solve it by applying inverse kinematics.

To this end, first, the foot-skating cleanup unit 134 selects all continuous frames where the foot contacts the ground. Each foot position in this frame range may be fixed to an average foot position of contact frames. Additionally, to smoothly connect adjacent motions at two boundaries of contact areas, the foot-skating cleanup unit 134 may apply the motion mixer window of 0.3 sec in two directions at the boundaries. Accordingly, the foot-skating cleanup unit 134 may output consistent, natural motion transformation result data through the output unit 140.

Figure 5:
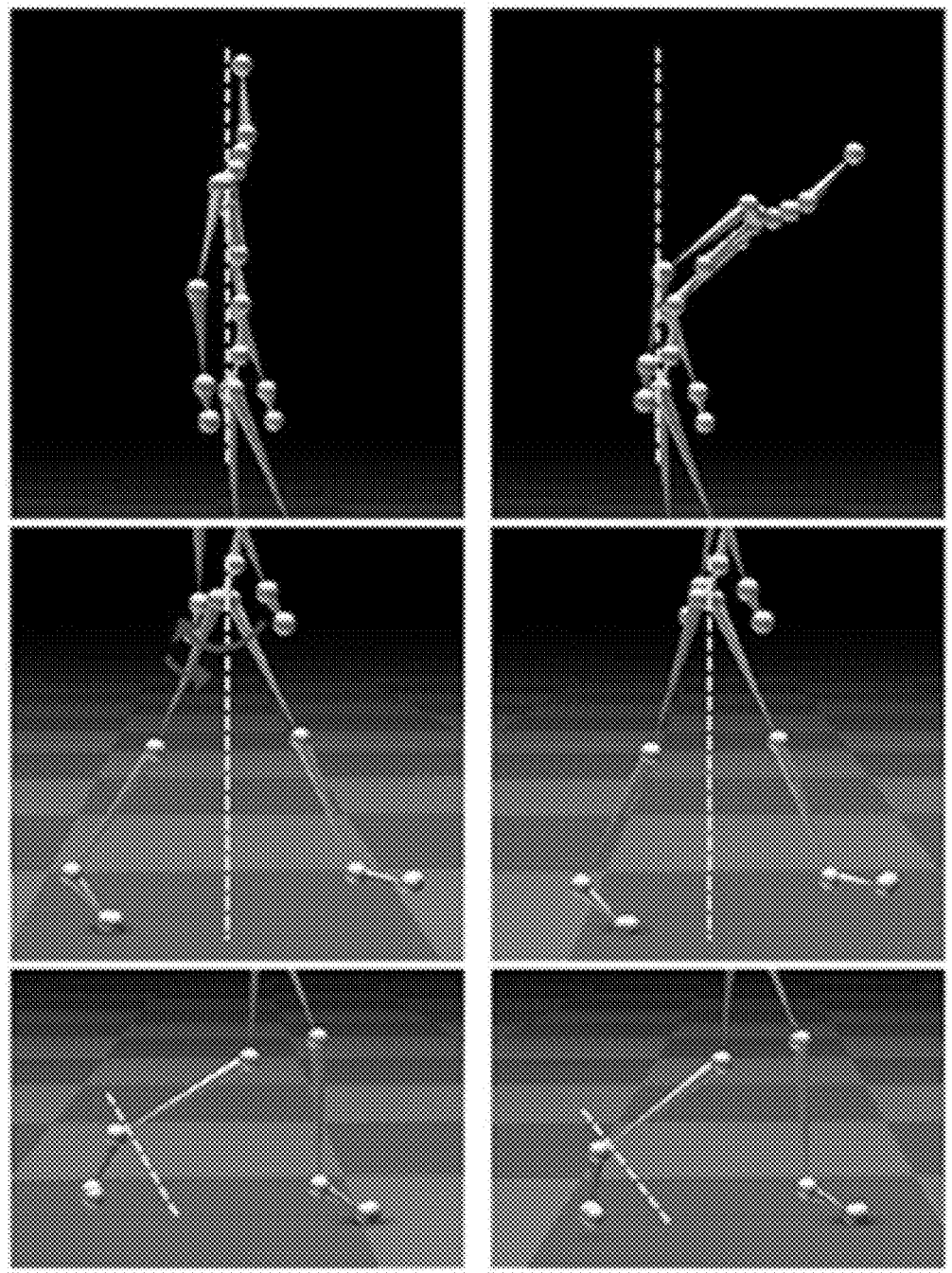
FIGS. 5 to 7 are diagrams illustrating the test results of motion transformation according to an embodiment of the present disclosure.
Figure 6:
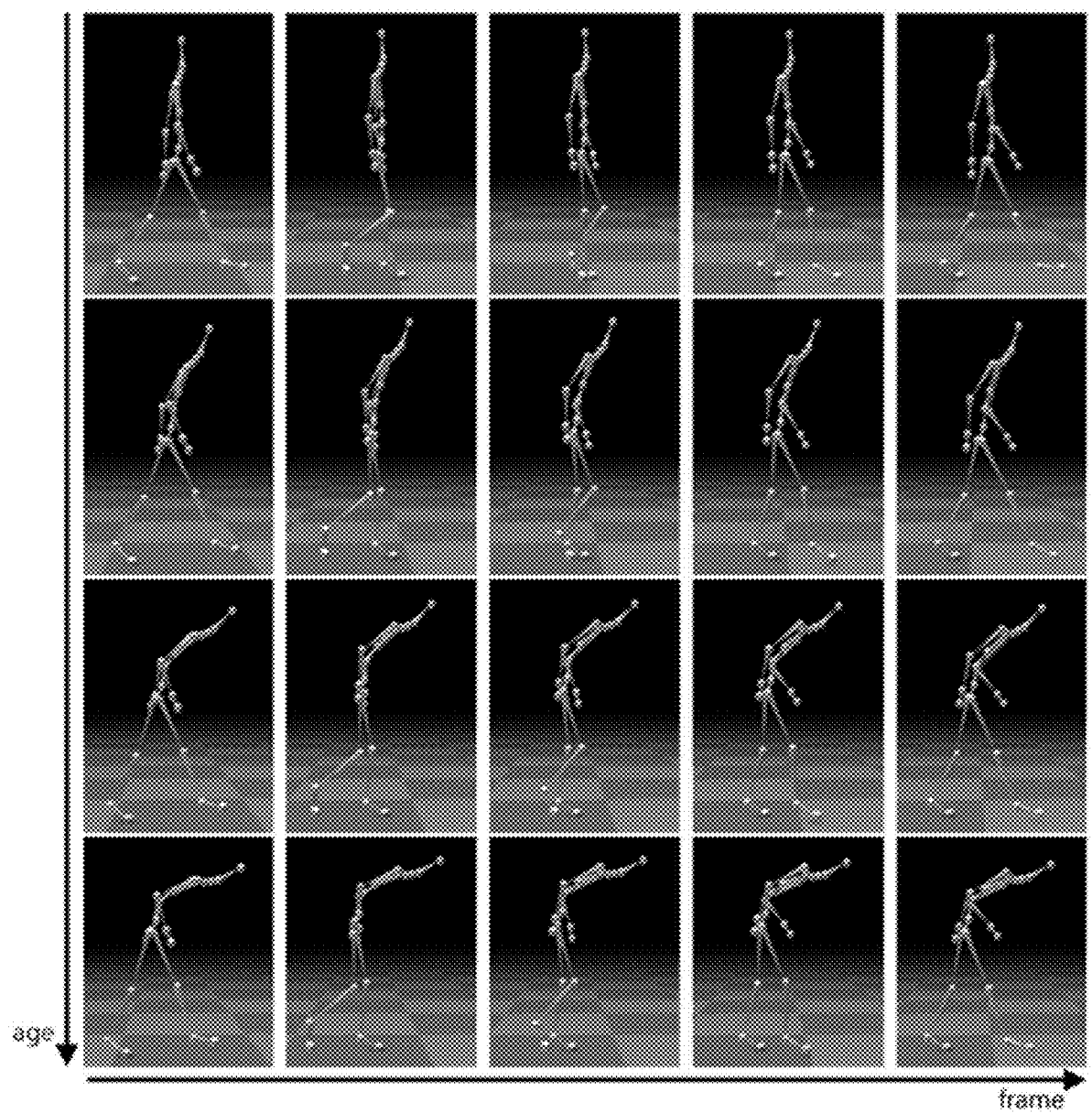
Figure 7:
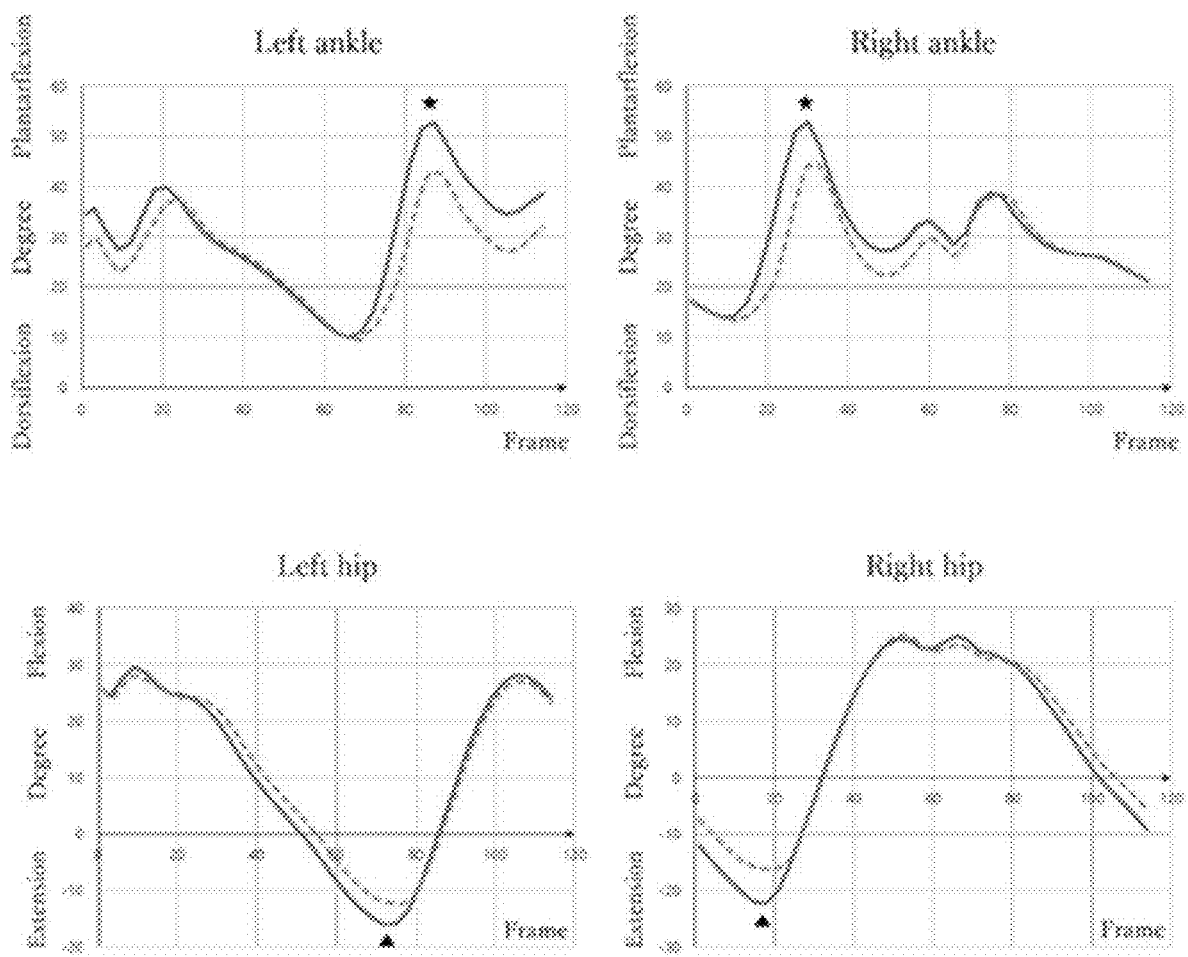

FIGS. 5 to 7 are diagrams illustrating the test results of motion transformation according to an embodiment of the present disclosure.

Referring to FIGS. 5 to 7, first, for basic data, gait motions of a 23-year-old person were captured to prepare motion data first. He was instructed to walk in various styles such as normal walk, strutting, sad and drunken walks.

Motions were captured using a Vicon motion capture system with 120 Hz Mx-40 eight cameras. Additionally, a skeleton character made up of 28 joints and 84 DoF was created, and all target changed motions were reproduced at 24 frames per second. The computation time results are as shown in the following Table 3.

TABLE 3

| Gait motion | Num. of frames | Time (s) |
| --- | --- | --- |
| Normal walk | 1200 | 37.889 |
| Strutting | 330 | 9.692 |
| Sad | 480 | 14.289 |
| Drunken | 360 | 10.708 |
| Aging from 23 to 100 | 800 | 28.797 |

As a result of experiment according to an embodiment of the present disclosure, it can be seen that the motion transformation apparatus 100 transforms gait motions quickly according to various input ages.

Table 3 shows the total calculation time of the entire process of motion transformation for generating age-related motion, and particularly, the last line shows transformation and reproduction timing of the character who gets older and older while walking. It can be seen that the system calculates 32.14 frames per second on average and can attain real-time performance.

FIG. 5 is an experimental result screen-shot showing a comparison of gait motions related to different age ranges. The left column shows motions captured from a 23-year-old man, and the right column shows gait motions of an 80-year-old person synthesized using the motion transformation apparatus 100. To show the age-related effects more clearly, yellow dash lines were inserted. It can be seen that in the first and second lines, the line is perpendicular to the ground, and in the third line, the line is perpendicular to the calf.

More specifically, referring to FIG. 5, the first line shows the effects of spinal posture changes with aging. The distorted spinal posture is clearly shown on the right side. The second line shows joint changes at the peak hip extension angle. In the second line, the effects of reduction in extension angle of hip joint and increase in anterior pelvic tilt can be simultaneously observed. In the left picture of the second line, the red counterclockwise arrow and the red clockwise arrow respectively indicate the reduced peak hip extension angle and the increased anterior pelvic tilt. As a result, the stride length of the elderly character is shorter than that of the younger character.

The third line shows ankle joints at the peak ankle plantarflexion angle, and it can be seen that the angle related to the elderly character is smaller than the angle related to the younger character. Here, it can be seen that the peak ankle plantarflexion angle reduces with aging. The trajectory of each value of the joint is shown in FIG. 7.

FIG. 6 shows outputs corresponding to different input ages over many frames, in which each line and column depicts each motion generated for the same instance, according to motions and gaits in various ages.

The motion of the first line shows basic motion data captured from a 23-year-old man. The remaining lines show the results outputted in an order of 50, 80 and 100 according to the input age. Although FIG. 6 uses biomechanical study of people aged 20-80 years on average, the embodiment of the present disclosure can be applied to ages over this age range. Often, it may be very useful for animations in which exaggeration is more valuable than accuracy.

As described above, only if basic motion data is acquired, it will be an easier alternative to a situation in which it is impossible to find an actor/actress over a specific age, or labor intensive conventional key frame or motion capture.

Particularly, like FIG. 6, this picture clearly shows automatic generation of many age-related features such as anteriorly tilting spine, reduced peak ankle plantarflexion symmetry and hip extension angle.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. An apparatus for motion transformation based on biomechanical observations, comprising:
   a basic data input unit through which basic motion data is inputted, the basic motion data including age information;
   an age input unit for receiving motion transformation age input information;
   a pre-processing unit which acquires a gait motion parameter through pre-processing of the inputted basic motion data;
   a motion transformation unit which performs biomechanical observations-based gait motion transformation processing, based on the pre-processed parameter, and a difference between the age information of the basic motion data and the motion transformation age input information; and
   an output unit which outputs the transformation processed motion.

2. The apparatus for motion transformation based on biomechanical observations of claim 1, wherein the pre-processing unit segments a gait motion of a character for the basic motion data by each gait cycle, and acquires a corresponding parameter.

3. The apparatus for motion transformation based on biomechanical observations of claim 1, wherein the motion transformation unit comprises a postural deformation unit to deform spine information of the basic motion data, corresponding to the age input information.

4. The apparatus for motion transformation based on biomechanical observations of claim 1, wherein the motion transformation unit comprises a timing adjustment unit to adjust motion timing of the basic motion data, corresponding to the age input information.

5. The apparatus for motion transformation based on biomechanical observations of claim 4, wherein the timing adjustment unit adjusts a gait speed according to the age input information.

6. The apparatus for motion transformation based on biomechanical observations of claim 4, wherein the timing adjustment unit adjusts time information of double support phase where both feet of the character contact the ground according to the age input information.

7. The apparatus for motion transformation based on biomechanical observations of claim 4, wherein the motion transformation unit comprises a joint angle optimization unit to calculate an optimized joint angle according to an objective function.

8. The apparatus for motion transformation based on biomechanical observations of claim 7, wherein the objective function includes a first variable term (Ea) for adjusting the joint angle according to the age input information by applying a weight, a second variable term (Ep) for preventing the transformed motion from changing by a predetermined size or more from the basic motion data, and a third variable term (Es) for smoothly processing changes in continuous frames.

9. The apparatus for motion transformation based on biomechanical observations of claim 1, further comprising a foot-skating cleanup unit to clean up foot-skating of data transformed and outputted from the motion transformation unit,
   wherein the clean up is performed by fixing a foot position over two or more frames of video,
   wherein the clean up is performed by inverse kinematics.

10. A method for motion transformation based on biomechanical observations, comprising:
    inputting basic motion data, the basic motion data including age information;
    inputting motion transformation age input information;
    acquiring a gait motion parameter through pre-processing of the inputted basic motion data;
    performing biomechanical observations-based gait motion transformation processing, based on the pre-processed parameter, and a difference between the age information of the basic motion data and the motion transformation age input information; and
    outputting the transformation processed motion.

11. The method for motion transformation based on biomechanical observations of claim 10, wherein the step of acquiring comprises segmenting a gait motion of a character for the basic motion data by each gait cycle, and acquiring a corresponding parameter.

12. The method for motion transformation based on biomechanical observations of claim 10, wherein the step of performing transformation processing comprises deforming spine information of the basic motion data, corresponding to the age input information.

13. The method for motion transformation based on biomechanical observations of claim 12, wherein the step of performing transformation processing further comprises, after the step of deforming, adjusting motion timing of the basic motion data, corresponding to the age input information, wherein a gait speed is adjusted according to the age input information or time information of double support phase where both feet of the character contact the ground is adjusted according to the age input information.

14. The method for motion transformation based on biomechanical observations of claim 13, wherein the step of performing transformation processing comprises, after the step of adjusting, calculating an optimized joint angle according to an objective function, wherein the objective function includes a first variable term (Ea) for adjusting the joint angle according to the age input information by applying a weight, a second variable term (Ep) for preventing the transformed motion from changing by a predetermined size or more from the basic motion data, and a third variable term (Es) for smoothly processing changes in continuous frames.

15. The method for motion transformation based on biomechanical observations of claim 14, further comprising cleaning up foot-skating of data transformed and outputted by inverse kinematics, wherein the cleaning up is performed by fixing a foot position over two or more frames of video,
wherein the cleaning up is performed by inverse kinematics.

\* \* \* \* \*